(12) United States Patent
Asculai

(10) Patent No.: US 8,758,819 B2
(45) Date of Patent: Jun. 24, 2014

(54) COSMETIC COMPOSITIONS FOR THE TREATMENT OF SKIN AND METHODS THEREOF

(75) Inventor: Samuel Asculai, Toronto (CA)

(73) Assignee: Enhance Skin Products, Inc., Toronto (CA)

(*) Notice: Subject to any disclaimer, the term of this patent is extended or adjusted under 35 U.S.C. 154(b) by 318 days.

(21) Appl. No.: 12/439,811

(22) PCT Filed: Sep. 7, 2007

(86) PCT No.: PCT/CA2007/001565
§ 371 (c)(1),
(2), (4) Date: Mar. 3, 2009

(87) PCT Pub. No.: WO2008/031194
PCT Pub. Date: Mar. 20, 2008

(65) Prior Publication Data
US 2010/0003340 A1    Jan. 7, 2010

Related U.S. Application Data

(60) Provisional application No. 60/844,085, filed on Sep. 13, 2006.

(51) Int. Cl.
| | | |
|---|---|---|
| A61K 9/14 | (2006.01) | |
| A61K 33/00 | (2006.01) | |
| A61K 33/06 | (2006.01) | |
| A61K 31/74 | (2006.01) | |
| A61K 8/73 | (2006.01) | |
| A61Q 19/08 | (2006.01) | |
| A61K 8/25 | (2006.01) | |

(52) U.S. Cl.
CPC . A61K 8/25 (2013.01); A61K 8/735 (2013.01); A61Q 19/08 (2013.01)
USPC ......... 424/488; 424/682; 424/600; 424/78.03

(58) Field of Classification Search
USPC .............................. 424/488, 682, 600, 78.03
See application file for complete search history.

(56) References Cited

U.S. PATENT DOCUMENTS

| | | | |
|---|---|---|---|
| 2,583,096 A | 1/1952 | Hadidian et al. | |
| 3,436,454 A | 4/1969 | Nouvel | |
| 3,887,703 A | 6/1975 | Manoussos et al. | |
| 4,141,973 A | 2/1979 | Balazs | |
| 4,272,522 A | 6/1981 | Balazs | |
| 4,303,676 A | 12/1981 | Balazs | |
| 4,582,865 A | 4/1986 | Balazs et al. | |
| 4,636,524 A | 1/1987 | Balazs et al. | |
| 4,684,627 A | 8/1987 | LeVeen et al. | |
| 4,711,780 A | 12/1987 | Fahim | |
| 4,716,224 A | 12/1987 | Sakurai et al. | |
| 4,725,585 A | 2/1988 | Wenge et al. | |
| 4,736,024 A | 4/1988 | Della Valle et al. | |
| 4,755,544 A | 7/1988 | Makino et al. | |
| 4,784,990 A * | 11/1988 | Nimrod et al. ................ 514/54 |
| 4,795,741 A | 1/1989 | Leshchiner et al. | |
| 4,801,619 A | 1/1989 | Lindblad | |
| 4,808,576 A | 2/1989 | Schultz et al. | |
| 4,814,176 A | 3/1989 | Makino et al. | |
| 4,840,941 A | 6/1989 | Ueno et al. | |
| 4,851,521 A | 7/1989 | della Valle et al. | |
| 4,853,226 A | 8/1989 | Machida et al. | |
| 4,900,550 A | 2/1990 | Lowry | |
| 4,937,254 A | 6/1990 | Sheffield et al. | |
| 4,946,870 A | 8/1990 | Partain, III et al. | |
| 4,957,744 A | 9/1990 | della Valle et al. | |
| 4,965,353 A | 10/1990 | della Valle et al. | |
| 4,970,298 A | 11/1990 | Silver et al. | |
| 4,988,503 A * | 1/1991 | Macchio et al. ................ 424/63 |
| 5,095,037 A | 3/1992 | Iwamitsu et al. | |
| 5,166,331 A | 11/1992 | della Valle et al. | |
| 5,639,738 A | 6/1997 | Falk et al. | |
| 5,792,753 A | 8/1998 | Falk et al. | |
| 5,824,658 A | 10/1998 | Falk et al. | |
| 5,827,834 A | 10/1998 | Falk et al. | |
| 5,830,882 A | 11/1998 | Falk et al. | |
| 5,852,002 A | 12/1998 | Falk et al. | |
| 5,910,489 A | 6/1999 | Falk et al. | |
| 5,914,322 A | 6/1999 | Falk et al. | |
| 5,929,048 A | 7/1999 | Falk et al. | |
| 5,932,560 A | 8/1999 | Falk et al. | |
| 5,942,498 A | 8/1999 | Falk et al. | |
| 5,962,433 A | 10/1999 | Falk et al. | |
| 5,972,906 A | 10/1999 | Asculai et al. | |
| 5,977,088 A | 11/1999 | Harper et al. | |
| 5,985,850 A | 11/1999 | Falk et al. | |
| 5,990,096 A | 11/1999 | Asculai et al. | |
| 6,017,900 A | 1/2000 | Falk et al. | |
| 6,048,844 A | 4/2000 | Falk et al. | |
| 6,069,135 A | 5/2000 | Falk et al. | |
| 6,087,344 A | 7/2000 | Falk et al. | |
| 6,103,704 A | 8/2000 | Falk et al. | |
| 6,114,314 A | 9/2000 | Falk et al. | |
| 6,136,793 A | 10/2000 | Falk et al. | |
| 6,140,312 A | 10/2000 | Falk et al. | |
| 6,147,059 A | 11/2000 | Falk et al. | |
| 6,159,955 A | 12/2000 | Asculai et al. | |
| 6,194,392 B1 | 2/2001 | Falk et al. | |

(Continued)

FOREIGN PATENT DOCUMENTS

| | | |
|---|---|---|
| AU | 30806/84 | 2/1985 |
| AU | 72117/87 | 12/1987 |

(Continued)

OTHER PUBLICATIONS

Santoianni, et al., Dermatology Online Journal, 2004, vol. 10(2):24.

(Continued)

*Primary Examiner* — Abigail Fisher
(74) *Attorney, Agent, or Firm* — Husch Blackwell LLP

(57) ABSTRACT

A cosmetic composition comprising at least one compound selected from bioactive/biocompatible microparticulates such as bioactive glass or bioactive ceramics, and an intradermal delivery vehicle selected from the group consisting of hyaluronans, hyaluronic acid and/or salts thereof and/or homologues, analogues, derivatives, complexes, esters, fragments and subunits of hyaluronic acid in an amount sufficient to facilitate deposition and penetration of said bioactive microparticulates through tissue at a site to be treated.

41 Claims, 2 Drawing Sheets

(56) References Cited

U.S. PATENT DOCUMENTS

| | | | |
|---|---|---|---|
| 6,218,373 | B1 | 4/2001 | Falk et al. |
| 6,281,195 | B1 * | 8/2001 | Rueger et al. ............. 424/423 |
| RE37,727 | E | 6/2002 | Hind |
| 6,509,322 | B2 | 1/2003 | Benedetti et al. |
| 6,517,863 | B1 * | 2/2003 | LaTorre et al. ............. 424/447 |
| 7,171,264 | B1 | 1/2007 | Hofmann et al. |
| 2002/0086039 | A1 * | 7/2002 | Lee et al. ............. 424/401 |
| 2007/0196312 | A1 | 8/2007 | Gross |

FOREIGN PATENT DOCUMENTS

| | | |
|---|---|---|
| AU | 14534/88 | 11/1988 |
| AU | 17459/88 | 12/1988 |
| CA | 1205031 | 5/1986 |
| CA | 1240929 | 8/1988 |
| CA | 2009730 | 2/1990 |
| CA | 2031880 | 6/1991 |
| DE | 2364373 | 7/1975 |
| EP | 0138572 | 4/1985 |
| EP | 0179442 | 4/1986 |
| EP | 0197718 | 10/1986 |
| EP | 0208623 | 1/1987 |
| EP | 0216453 | 4/1987 |
| EP | 0224987 | 6/1987 |
| EP | 0240098 | 10/1987 |
| EP | 0244178 | 11/1987 |
| EP | 0265116 | 4/1988 |
| EP | 0270317 | 6/1988 |
| EP | 0285357 | 10/1988 |
| EP | 0287210 | 10/1988 |
| EP | 0295092 | 12/1988 |
| EP | 0296740 | 12/1988 |
| EP | 0312208 | 4/1989 |
| EP | 0341745 | 11/1989 |
| EP | 0378852 | 7/1990 |
| EP | 0 626 863 | 12/1994 |
| EP | 0 445 255 | 12/1995 |
| EP | 0769287 | 4/1997 |
| EP | 0 839 052 | 5/2002 |
| EP | 1206933 A1 * | 5/2002 |
| EP | 1253903 B1 | 11/2002 |
| GB | 1283892 | 8/1972 |
| GB | 2099826 | 12/1982 |
| JP | 57183707 | 11/1982 |
| JP | 61000017 | 1/1986 |
| JP | 62201825 | 9/1987 |
| JP | 62287041 | 12/1987 |
| JP | 2002-80358 | 3/2002 |
| WO | WO 88/07060 | 9/1988 |
| WO | WO 89/07932 | 9/1989 |
| WO | WO 91-04058 | 4/1991 |
| WO | WO 9117777 A2 * | 11/1991 |
| WO | WO 01/72262 | 8/2001 |
| WO | WO 2007/024810 A2 | 3/2007 |

OTHER PUBLICATIONS

Pillai, et al., International Journal of Cosmetic Science, Oct. 2005, vol. 27, Issue 5.
International Search Report related to PCT/CA2007/001565.
Decarufel, Laura, Acid trip: The science of good skin; www.ellecanada.com; (2011). (2 pages).
Hyaluronan from Wikipedia; (2011) (13 pages).
Meyer et al., The Polysaccharide of the Vitreous Humor; The Jounrnal of Biological Chemistry, 107, (Dec. 1, 1934); pp. 629-634.
Vitryxx HA Serum, A new, effective and easy-to-formulate Anit-Aging Ingredient; Product Information; Schott glass made of ideas' (2011) (2 pages).
Schott Vitryxx Bioactive Glass for skin care; Product Information; Schott glass made of ideas (2011) (2 pages).
Pigman, et al., "Acide Hyaluronique et facteurs de permeabilite tissulaire", Bull. Soc. Chim. Biol., 1963, 45(2-3), pp. 185-202.
Seroli, et al., "L'acido jaluronico, peruso topico, nella cura delle ulcere trofocircolatorie degli arti inferiori", (Comunicazioni), Giornale Italiano di Dermatologia, 1970, 45(8) pp. 468-471.
Walther, M., The prevention of strine cutis distansae during pregnancy, Mineva Gynecolgia, 1981, vol. 33, pp. 497-499.
Kelley, RS, et al., Complete spontaneous regression of multiple basal cell carcinomas in basal cell nevus syndrome: Possible role of transepithelial elimination, J. Dermatol. Surg. Oncol. 16(11) pp. 1039-1042, 1990.
Reynolds, et al., "Martindale The Extra Pharmacopoeia", The Pharmaceutical Press, London, pp. 234-235 (1982).
West, et al., 1989, Exp. Cell Res., 183, 179-196.
Alho, et al., 1989, J. Cell Biol. 108, 1557-1565.
Blakeslee, "Solid cores of tumors keeping out best drugs", Jul. 8, 1989 edition of the Globe and Mail, Toronto, Ontario, p. D4.
Harrison, "Toxic drug tamed but still potent", Ontario Medicine, vol. 8, No. 16, dated Aug. 21, 1989, p. 1.
The Merck Index Eleventh Edition, Centennial Edition, Hyaluronic acid formulation, pp. 751 and 752, 1989.
Braun, D.P., et al, Alan R. Liss, Inc., Modulation of immunity in cancer patients by prostaglandin antagonists, Immunity to Cancer II, 1989, pp. 439-448.
Goodwin, J.S. Prostaglandin E and cancer growth potential for immunotherapy with prostaglandin synthesis inhibitors, Augmentive Agents in Cancer Therapy, Raven Press, New York, pp. 393-415 (1981).
Acsulai, Samuel, "Inactivation of herpes simplex viruses by nonionic surfactants", Antimicrobial Agents and Chemotherapy, Apr. 1978, pp. 686-690.
Sneader, Chemical Abstracts, vol. 76, No. 10, "Possible mechanism for action of DMSO on percutaneous Absorption", J. Pharm. Pharmcol. 1971, 23 (Supp).
Alaverdyan MI, Ter-Avetisyan AT, Effect of hyaluronidase, hyaluronic acid, and some other substances on postradiational experimental bacteriemai, Bulletin of Experimental Biology and Medicine, 1967(9), pp. 967-969.
Balazs, EA, Gibbs, DA, The rheological properties and biological function of hyaluronic acid, In: Chemistry and Molecular Biology of the Intercellular Matrix, vol. III, New York, Academic Press, 1970, pp. 1241-1253.
Balazs EA, Band P., Hyaluronic acid: Its structure and use, Cosmetics & Toiletries, Polymers in Cosmetics, 1984; 99, pp. 65-72.
Camber O, Lundgren P., Diffusion of some low molecular weight compounds in sodium hyaluronate, Acta Pharmaceutica Suecica, 1985, 22(6), pp. 315-320.
Camber, O., Edman, P., Gurny, R., Influence of sodium hyaluronate on the meiotic effect of pilocarpine in rabbits, Current Eye Research, 1987, 6(6), pp. 779-784.
Chang, S-C, Pro-drug and vehicle approaches to improve the therapeutic index of topically applied timolol in the pigmented rabbit, Dissertation Abstracts International, 1988, 49(2), 367-B.
Cravioto, R.O, et al., Effects of precipitates formed by insulin with hyaluronic acid and mucoid from vitreous humor in depressing blood-sugar levels, Science, 1950, vol. III, pp. 520-521.
Gieldanowski, et al., Studies on immunosuppressive and anti-inflammatory effect of adriamycin, Arch. Immunol. Ther. Exp, 1980, 28(3), pp. 439-446.
Hassan, et al., Effects of adjuvants to local anaesthetics on their duration, Acta Anaesthesiol. Scand., 1985, 29, pp. 384-388.
Hurd, ER, Immunosuppressive and anti-inflammatory properties of cyclophosphamide, azathioprine and methotrexate, Arthritis and Rheumatism (Jan.-Feb. 1973); 16(1), pp. 84-88.
Idson, B., Polymers in skin cosmetics, Cosmetics & Toiletries, 1988, 103, pp. 63-68.
Johansson, et al., Effects of adjuvants to local anaesthetics on their duration, Acta Anaesthesiol Scand., 1985, 29, pp. 736-738.
Kalbhen, D.A., The inhibitory effects of steroidal and non-steroidal antirheumatic drugs on articular cartilage in osteoarthrosis and its counteraction by a biological GAG-peptide complex (Rumalon®), Z. Rheumatol, 1982, 41, pp. 202-211.
Kreis, et al., Nonsteroidal anti-inflammatory agents as a substitute treatment for steroids in ATGAM-treated cadaver kidney recipients, Transplantation, Feb. 1984, 37(2), pp. 139-145.

(56) References Cited

OTHER PUBLICATIONS

McIlwraith, E., Current concepts in equine degenerative joint disease, Journal of the *American Veterinary Medical Association*, Feb. 1, 1982, pp. 239-250.

Nizolek, et al., "Corticosteroid and hyaluronic acid treatments in equine degenerative joint disease: A review", *The Cornell Veterinarian*, 1981, 71(4), 355-375.

Pruett, et al., Hyaluronic acid viteous substitute. In: *Vetreous surgery and advances in fundus diagnosis and treatment*, Freeman H.M., et al., Editors, Appleton-Century-Crofts, 1977, Chapter 55, pp. 433-444.

Reim, et al., Surgical procedures in the treatment of most sever eye burns, *Acta Ophthalmologica*, 1989, Supplementum 192, pp. 67, 47-54.

Rydell, et al., Effect of intra-articular injection of hyaluronic acid on the clinical symptoms of osteoarthritis and on granulation tissue formation, *Clinical Orthopaedics and Related Research*, 1971; 80(Oct.), pp. 25-29.

Saba, et al., Investigation of the antihyperlipemic activity of an association of clofibrate and extractive mucopolysaccharide complex, *Current Therapeutic Research*, 1978, 23(4), pp. 455-463.

Stegman, et al., Use of sodium hyaluronate in severe penetrating ocular trauma, *Acta Ophthalmol*, 1986, 18, pp. 9-13.

Trabucchi, et al., Prevention of wound dehiscence in severely obese patients with jejuno-ileal by-pass: The role of hyaluronic acid, *Pharmatherapeutica*, 1988, 5(4), pp. 233-239.

Weirich, et al., Dermatopharmacology of salicylic acid. III. Topical contra-inflammatory effect of salicylic acid and other drugs in animal experiments, *Dermatologica*, 1976, 152, pp. 87-99.

Office Action for related Japanese Application No. 2009-527658 dated Jan. 22, 2013.

\* cited by examiner

% Improvement in Skin Texture, Evenness and Luminance at Week 2 and 4

% of Subjects Showing Improvement from Baseline

COSMETIC COMPOSITIONS FOR THE TREATMENT OF SKIN AND METHODS THEREOF

FIELD OF THE INVENTION

The present invention relates generally to cosmetic compositions and more specifically it relates to a cosmetic composition for the treatment of skin after non ablative skin rejuvenation procedures. The composition is intended to reduce inflammation, enhance and accelerate healing, inhibit infection, enhance skin tone and moisturize.

BACKGROUND OF THE INVENTION

Description of the Related Art

It can be appreciated that cosmetic compositions have been in use for years. Typically, cosmetic compositions are comprised of creams, lotions, and various cosmeceutical formulations.

While cosmetic compositions comprising bioactive glasses are known to exist, there are no known composition which discloses a combination of bioactive glass and an intradermal delivery system which facilitates and accelerates the healing of skin scarred by, for example, non-surgical ablative skin resurfacing procedures.

Known in the art are intradermal delivery methods of active agents by needle-free injection and electroporation. For example, U.S. Pat. No. 7,171,264 discloses methods for introducing a biologically active agent into cells of a subject by introducing the agent in a form suitable for electrotransport into a region of tissue of the subject using one or more needle-free injectors, and applying a pulsed electric field to the region of tissue, thereby causing electroporation of the region of tissue. The patent discloses that the combination of needle-free injection and electroporation is sufficient to introduce the agent into cells in skin, muscle or mucosa.

Also known in the art are methods of Intradermal drug delivery by low frequency sonophoresis. Santoianni et al. describe such methods in their paper (Intradermal drug delivery by low frequency sonophoresis (25 KHz) Pietro Santoianni, Massimilano Nino, and Gabriella Calabro, Dermatology Online Journal 10 (2): 24). The use of low frequency sonophoresis enhances the penetration of topic agents obtaining effects at the level of the epidermis, dermis and appendages (intradermal delivery), giving better results in the treatment of some cosmetic skin disorders.

In the U.S. Pat. RE37,727, Hind, H. W. discloses methods for reducing nerve injury pain associated with shingles (herpes-zoster and post-herpetic neuralgia), where intradermal delivery of lidocaine is maintained for a predetermined period of time. The lidocaine appears to specifically affect the damaged nerve fibers, while leaving the undamaged and normal nerve fibers with retention of response to other stimuli. The lidocaine formulations allow for the necessary dosage of the lidocaine in the dermis during the period of treatment. The formulation may be covered with an occlusive or non-occlusive dressing, which protects the lidocaine formulation mechanical removal and enhances the transport of the lidocaine into the dermis. Long term relief is realized after maintenance of the administration of lidocaine has been terminated.

Hyaluronic acid has been taught and used previously for topical applications of drugs—See for example U.S. patents:

| | |
|---|---|
| 6,218,373 | Formulations containing hyaluronic acid |
| 6,194,392 | Treatment of conditions and disease |
| 6,159,955 | Use of hyaluronic acid and a NSAID for the manufacture of a medicament for the treatment of mucosal diseases |
| 6,147,059 | Formulations containing hyaluronic acid |
| 6,140,312 | Formulations containing hyaluronic acid |
| 6,136,793 | Formulations containing hyaluronic acid |
| 6,114,314 | Formulations containing hyaluronic acid |
| 6,103,704 | Therapeutic methods using hyaluronic acid |
| 6,087,344 | Formulations containing hyaluronic acid |
| 6,069,135 | Use of hyaluronic acid or its derivatives to enhance delivery of therapeutic agents |
| 6,048,844 | Treatment of conditions and disease |
| 6,017,900 | Topical composition containing hyaluronic acid and nsaids |
| 5,990,096 | Formulations containing hyaluronic acid |
| 5,985,850 | Compositions comprising hyaluronic acid and drugs |
| 5,977,088 | Formulations containing hyaluronic acid |
| 5,972,906 | Treatment of mucous membrane disease, trauma or condition and for the relief of pain thereof |
| 5,962,433 | Topical composition containing hyaluronic acid and NSAIDS |
| 5,942,498 | Formulations containing hyaluronic acid |
| 5,932,560 | Treatment of conditions and disease |
| 5,929,048 | Treatment of conditions and disease |
| 5,914,322 | Treatment of disease and conditions |
| 5,910,489 | Topical composition containing hyaluronic acid and NSAIDS |
| 5,852,002 | Treatment of conditions and disease |
| 5,830,882 | Compositions containing a form of hyaluronic acid and a medicinal agent for treating acne in mammals and methods for administration of such composition |
| 5,827,834 | Method of using hyaluronic acid or its pharmaceutically acceptable salts for the treatment of disease |
| 5,824,658 | Topical composition containing hyaluronic acid and NSAIDS |
| 5,792,753 | Compositions comprising hyaluronic acid and prostaglandin-synthesis-inhibiting drugs |
| 5,639,738 | Treatment of basal cell carcinoma and actinic keratosis employing hyaluronic acid and NSAIDs |

Also see European Patent Applications and Patents:
EP 839052 B1
EP 445255 A3
EP 626863 A1

In an article published Oct. 3, 2005, in International Journal of Cosmetic Science (Pillai, R.; Redmond, M., Roding, J., Anti-Wrinkle Therapy: Significant New Findings in the Non-Invasive Cosmetic Treatment of Skin Wrinkles with Beta-Glucan, International Journal of Cosmetic Science, October 2005, Volume 27, Issue 5) a study was identified which allegedly taught that oat beta glucan can penetrate the skin despite years of doctors and scientists believing that the large molecule was too big. It was asserted in the article that "Ceapro has also discovered that beta glucan can be used as a transdermal delivery system to feed drugs and other compounds into the skin. This development [speculated that the beta glucan] may lead to new and better ways of delivering such medicines as antihistamines and pain relievers."

The main problem with conventional cosmetic compositions is that they do not address the issues of treating skin after non-surgical, ablative skin resurfacing procedures such as chemical peels, microdermabrasion, laser peels, etc. Another problem with conventional cosmetic compositions is that they are not anti-inflammatory in nature. Another problem with conventional cosmetic compositions is that they do not promote healing.

In these respects, the cosmetic compositions for the treatment of skin according to the present invention substantially depart from the conventional concepts of the prior art, and in so doing provide a skin treatment primarily developed for the purpose of treating of skin after non ablative skin resurfacing procedures. The composition is intended to reduce inflammation, enhance and accelerate healing, inhibit infection, enhance skin tone and moisturize. The composition is also designed to reduce age-related changes in the production of pro-inflammatory cytokine and to prevent Th1-Th2 cytokine profile shift.

SUMMARY OF THE INVENTION

The cosmetic compositions of the present invention overcome disadvantages inherent in the known types of cosmetic compositions part of the prior art. According to one aspect of the present invention there is provided a new cosmetic composition for the treatment of skin wherein the same can be utilized for treatment of skin after non ablative skin resurfacing procedures. The composition is intended to reduce inflammation, enhance and accelerate healing, inhibit infection, enhance skin tone and moisturize.

Such a composition comprises a biocompatible microparticulate (ceramic/glass) and an intradermal delivery vehicle to reduce inflammation and redness after skin resurfacing procedures. Preferably the intradermal delivery vehicle comprise hyaluronic acid for example medical grade having an average molecule weight of the order of about 700 KiloDaltons.

Thus, an object of the present invention is to provide a novel cosmetic composition and treatment for the treatment of skin that has advantages discussed above.

The cosmetic composition according to the present invention for the treatment of skin that will overcome the shortcomings of the prior art compositions.

Another object of the present invention is to provide a cosmetic composition and treatment for the treatment of skin, for example, after non ablative skin resurfacing procedures. The composition is preferably intended to reduce inflammation of the skin tissue, enhance and accelerate healing of the skin tissue, inhibit infection, enhance skin tone and moisturize.

Another object of the invention is to provide a cosmetic composition and treatment for treatment of the face, neck and other areas after skin rejuvenation procedures such as chemical peels, skin resurfacing procedures such as microdermabrasion and non ablative laser and non laser procedures.

Another object is to provide a cosmetic composition and treatment for the treatment of skin that contains the natural moisturizing and wound healing molecule, hyaluronan. Preferably, the hyaluronan is present hyaluronic acid or salt thereof or a homologue, analogue, derivative, complex, ester, fragment and subunit of hyaluronic acid.

According to one aspect of the invention, there is provided a cosmetic composition comprising: at least one compound selected from bioactive/biocompatible microparticulates; and an intradermal delivery vehicle selected from the group consisting of: hyaluronans, hyaluronic acid and/or salts thereof and/or homologues, analogues, derivatives, complexes, esters, fragments and subunits of hyaluronic acid in an amount sufficient to facilitate deposition and penetration of said bioactive microparticulates through tissue at a site to be treated. Preferably, the intradermal delivery is hyaluronic acid. More preferably, the hyaluronic acid is of medical grade and has an average molecular weight of about 700 kiloDaltons.

Another object is to provide a cosmetic composition for the treatment of skin that contains both hyaluronan and bioactive microparticulates.

Another object is to provide a cosmetic composition and treatment for the treatment of skin that contains plant and/or animal extracts which enable the prevention of the Th1-Th2 cytokine profile shift and to neutralize free radicals within skin cells.

Such cosmetic compositions for the treatment of skin may, in addition to the above contain normally found cosmetic excipients such as oils, gums, glycerin, preservatives, water, etc.

Thus, it is the object of the present invention to provide novel cosmetic compositions and treatment which have the effect of fundamentally improving, maintaining or enhancing the protective and maintenance performance of normal skin after skin rejuvenation procedures. Preferably, the cosmetic compositions of the present invention which can reduce and treat skin roughness, inflammation, infection and moreover can assist to diminish dermal aging such as wrinkle formation as well as improve the water retaining ability of normal skin.

According to one aspect of the invention there is provided a method of treating skin which for example may have undergone a non-ablative rejuvenation procedure by using cosmetic compositions comprising bioactive/biocompatible microparticulates such as bioactive/biocompatible glass, and/or biocompatible microparticulates (ceramic glass) and an intradermal delivery vehicle (for example medical grade having an average molecule weight of in the order of about 700 kilo Daltons) selected from the group consisting of: hyaluronans, hyaluronic acid and/or salts thereof and/or homologues, analogues, derivatives, complexes, esters, fragments and subunits of hyaluronic acid sufficient to facilitate the bioactive microparticulates and/or biocompatible microparticulates (ceramic glass) deposition and penetration through the tissue (including scar tissue) at the site to be treated. This invention also provides the composition used in such treatment, additionally effective amounts may be taken from the composition and applied to the skin to enhance and accelerate healing of skin tissue, reduce erythema, moisturize and enhance skin tone.

According to another aspect of the present invention, the cosmetic composition may comprise hyaluronan and bioactive microparticulates such as bioactive glass bioactive ceramics, bioactive minerals and/or composites of these. The hyaluronan may preferably be comprised of hyaluronic acid, medical grade, for example having an average molecular weight of about 700 kiloDaltons. Preferably, the bioactive microparticulates may comprise bioactive glass 45% by weight Silicon Dioxide, 24.5% by weight Calcium Oxide, 24.5% by weight Disodium Oxide, 6% by weight Diphospho pentoxide <20 micrometers in diameter. Also preferably, the bioactive multiparticulates are a bioactive glass comprising 60 mol % $SiO_2$, 36 mol % CaO, and 4 mol % $P_2O_5$. Also preferably, bioactive multiparticulates comprise are bioactive glass which a bioactive glass comprising 70 mol % $SiO_2$, 30 mol % CaO.

An aspect of the invention provides for a method of treating skin comprising administering to the skin an effective amount of a cosmetic composition comprising hyaluronan and bioactive microparticulates, the microparticulates selected from the group consisting of: bioactive glass, bioactive ceramics, bioactive minerals and/or composites of these, the hyaluronan comprising medical grade hyaluronic acid, having an average molecular weight about 700 kiloDaltons. Preferably, an effective amount of the composition comprises at least 10 mg of the form of hyaluronic acid per square inch. Preferably the method is for treating skin after non-ablative skin rejuvenation procedures.

Also preferably, the method of treating skin according to the present invention accomplishes at least one of the following: reduce inflammation of skin tissue; enhance and accelerate healing of skin tissue; inhibit infection of skin tissue; enhance skin tone; and moisturize.

According to one aspect of the invention, there is provided a cosmetic composition comprising about 96.6% water; 0.5% sodium hyaluronate; 0.95% calcium, sodium phosphosilicate; 0.9% citric acid; 0.8% phenoxyethanol; 0.2% methylparaben; and 0.05% mica.

According to another aspect of the invention, there is provided a composition for administration to the human skin comprising of purified water 97.1%, Sodium Hyaluronate 0.5% (molecular weight in the order of above 700 kilo Daltons), Calcium Sodium Phosphosilicate 0.95%, Citric Acid 0.9%, Mica 0.05%, and Methyl parabens/phenoxyethanol 0.5%.

According to one aspect of the invention, there is provided a cosmetic composition comprising a bioactive/biocompatible microparticulate and an intradermal delivery vehicle. Preferably, the intradermal delivery vehicle is hyaluronic acid of medical grade and has an average molecular weight of about 700 kiloDaltons.

Other objects and advantages of the present invention will become apparent to the skilled person as he/she understands this document. It is thus intended that these objects, features and advantages are within the scope of the present invention.

BRIEF DESCRIPTION OF THE DRAWINGS

The following figures illustrate preferred and alternative embodiments of the invention, wherein.

DETAILED DESCRIPTION OF THE INVENTION

Figure 1:
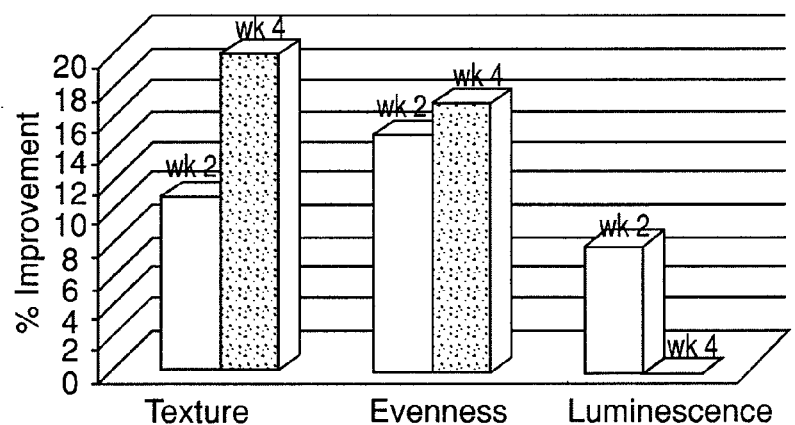
FIG. 1 is a graph which summarizes improvements in skin texture, evenness and luminance after 2 weeks and 4 weeks after using the product according to the present invention.

A cosmetic composition for the treatment of skin is comprised of an intradermal delivery vehicle which is preferably a hyaluronan and bioactive microparticulates such as bioactive glass. In an embodiment of the present invention, hyaluronic acid, medical grade, average molecular weight of about 700 kiloDaltons is used. In another embodiment, the bioactive microparticulate may be a bioglass which is comprised of: 45% by weight Silicon Dioxide, 24.5% by weight Calcium Oxide, 24.5% by weight Disodium Oxide, 6% by weight Diphospho pentoxide the bioactive microparticulate is preferably in a size less than 20 micrometers in diameter may be included.

In another embodiment, hyaluronic acid, medical grade having an average molecular weight of 700 kiloDaltons or salts thereof may be used and/or homologues, analogues, derivatives, complexes, esters, fragments and subunits of hyaluronic acid may be used. The amount of hyaluronan must preferably be such that it is sufficient to facilitate the bioactive glass deposition and penetration through the tissue (including scar tissue) at the site to be treated.

Effective amounts may be applied (such as at least about 10-15 mg of the form of hyaluronic acid) for application to the skin's surface (for example per square inch (per 6.25 sq. cm.)) to enhance and accelerate healing, reduce erythema, moisturize and enhance skin tone.

It is believed that high purity hyaluronic acid and/or salts thereof (such as the sodium salt) and/or homologues, analogues, derivatives, complexes, esters, fragments and/or subunits of hyaluronic acid of the molecular weight referenced above is sufficient to exert all the effects listed above. Preferably high purity hyaluronic acid or salts thereof are employed. Preferably the composition contains 45% by weight Silicon Dioxide, 24.5% by weight Calcium Oxide, 24.5% by weight Disodium Oxide, 6% by weight Diphospho pentoxide <20 micrometers in diameter. Bioactive glasses are known mainly as bone grafting materials. Their beneficial biological activity and high level of biocompatibility are well documented. Recent demonstrations that finely grained powders of bioactive glasses have substantial anti-microbial, anti-inflammatory and mineralizing properties have led to this invention that these are suited to function as active ingredients for use in a broad variety of cosmetic and personal care products. As a material, glass is a collective term of an unlimited number of different compositions in a glassy or amorphous state. As opposed to crystalline materials, glasses do not have a long range order in their molecular network but have a more random structure. While constituents and compositional ranges may vary, bioactive glasses are typically composed of oxides of silicon, calcium, sodium and phosphorus. In the form that is approved for medical use, and for which the bulk of the safety and efficacy data exist, the composition is 45% by weight $SiO_2$, 24.5% by weight $CaO$, 24.5% by weight $Na_2O$, 6% by weight $P_2O_5$. Suitable bioactive glasses include but are not limited to:

(a) 60 mol % $SiO_2$, 36 mol % $CaO$, 4 mol % $P_2O_5$; and
(b) 70 mol % $SiO_2$, 30 mol % $CaO$.

Suitable compositions may thus comprise the following:

(a) a bioactive glass comprising 60 mol % $SiO_2$, 36 mol % $CaO$, 4 mol % $P_2O_5$; and
(b) a bioactive glass comprising 70 mol % $SiO_2$, 30 mol % $CaO$.

Though its mechanism of action is not fully understood, it is believed that hyaluronan interacts with the bioglass surface when the bioglass is suspended in the hyaluronan. When this suspension is applied to the skin, the hyaluronan facilitates the penetration of the bioactive glass into the stratum corneum and into the epidermis where the hyaluronan anchors the bioactive glass to the cells through the interaction of hyaluronan and its hyaladherin receptors and reduces inflammation, reduces erythema, texturizes the skin, improves skin elasticity, reduces fine lines and wrinkles, reduces pore size, and hydrates the skin.

The composition described can be in a lotion form, cream form or a gel. The bioactive microparticulates may be bioactive glasses, bioactive ceramics, bioactive minerals or composites of these.

Such cosmetic compositions for the treatment of skin may, in addition to the above contains normally found cosmetic excipients such as oils, gums, glycerin, preservatives, water, etc.

The present invention relates to cosmetic compositions for the treatment of the face, neck and other areas, for example, after skin rejuvenation procedures such as chemical peels, skin resurfacing procedures such as microdermabrasion and non ablative laser and non laser procedures.

When effective amounts of these compositions are applied to the skin it is believed that they accelerate the reduction of erythema, accelerate healing, exert anti-inflammatory and anti-microbial effects, enhance water retention in the epidermis/dermis and have unexpected effects in reducing skin roughness, improving skin tone and preventing the formation of wrinkles.

The cosmetic compositions may, for example, be applied to the area which has undergone skin rejuvenation procedures. Results, we expect, are apparent within sixty minutes after application.

The following non-limiting examples further illustrate the invention.

Example 1

One such exemplary composition comprises:

|  | Percentage (%) |
| --- | --- |
| Water | 96.6 |
| Sodium Hyaluronate | 0.5 |
| Calcium, Sodium Phosphosilicate | 0.95 |
| Citric Acid | 0.9 |
| Phenoxyethanol | 0.8 |
| Methylparaben | 0.2 |
| Mica | 0.05 |
|  | 100.00 |

The following study was carried out with the indicated formulation:

Study

The objective of the study is to determine if the use of a skin treatment product improved the following parameters of the skin:

the appearance of fine lines/wrinkles at the crow's feet area;
pore size;
skin texture;
evenness;
radiance;
elasticity;
moisture; and
the appearance of redness in a panel of 10 women, aged 40 years and older, fifteen (15) minutes following a single product application and after 2 and 4 weeks of product using clinical grading and VISIA-CR image analysis.

The following illustrates the formulation used:

| Purified water | 97.1% |
| --- | --- |
| Sodium Hyaluronate | 0.5% (molecular weight in the order of above 700 kiloDaltons) |
| Calcium Sodium Phosphosilicate | 0.95% |
| Citric Acid | 0.9% |
| Mica | 0.05% |
| Caprylyl Glycol | 0.5% |

Ethics

Ethical Conduct of the Study

This study was conducted in accordance with the intent and purpose of Good Clinical Practice regulations described in Title 21 of the U.S. Code of Federal Regulations (CFR), the Declaration of Helsinki and/or Essex Testing Clinic (ETC) Standard Operating Procedures (SOPs).

Subject Information and Consent

This study was conducted in compliance with CFR Title 21, Part 5 0 (Informed Consent of Human Subjects). Informed Consent was obtained from each subject in the study and documented in writing before participation in the study. A copy of the Informed Consent was provided to each subject.

Test Subjects

Ten (10) female subjects, ranging in age from 46 to 65 years, were empaneled for the home-use testing procedure.

Each panelist read, understood and signed a written Informed Consent Form and completed a brief Medical History Form.

Study Design

Subject Selection

A sufficient number of females, 40 years of age and older and in general good health, were empaneled so that approximately 10 would finish. All subjects were required to read, understand and sign an Informed Consent Form and to complete a brief Medical History Form.

Inclusion Criteria

1. Females aged 40 and older, in general good health.
2. Individuals with a fine line/wrinkle score of "5" (moderate) or greater at the crow's feet area.
3. Individuals with a pore-size score of "5" (medium-sized pores visible) or greater on the face.
4. Individuals who were regular users of moisturizers. (Moisturizer could not contain any AHAs, BHAs, retinoids or any other "anti-aging" treatments.)
5. Individuals who could read, understand and sign the Informed Consent form.
6. Individuals who anticipated ability the to complete the course of the study and to comply with instructions.

Exclusion Criteria

1. Women who were pregnant, planning a pregnancy, lactating and/or nursing a child.
2. Individuals with any visible skin disease which might have interfered with the evaluations.
3. Individuals engaged in a concurrent research project of a facial product.
4. Individuals taking medications might have interfered with the test results including the use of steroidal/non-steroidal anti-inflammatory drugs or antihistamines.
5. Individuals with acne, active atopic dermatitis/eczema or psoriasis.
6. Individuals that were currently under treatment for asthma or diabetes.
7. Individuals who had undergone a facelift or who had widespread facial scarring.
8. Individuals that smoked.
9. Individuals with a known sensitivity to cosmetics or personal care products.

Study Procedure

The study is designed as a 4-week study in which the test article was used by each of the test panelists according to the Sponsor's use instructions.

Subjects reported to the Testing Facility for the baseline visit. A trained technician evaluated the presence of crow's feet fine lines/wrinkles on the face of each subject and evaluated pore size. The elasticity of the skin was measured using the Cutometer® (Courage+ Khazaka, Germany) and the moisture content of the skin was measured using the Corneometer® (Courage+ Khazaka, Germany). Photographs were taken of the face using the Visia CR® Imaging System (Canfield Scientific, Fairfield, N.J.). Using the Image Pro® Software, the photographs were analyzed to determine changes (if any) in skin texture, evenness, radiance and redness. An irritation evaluation was conducted for safety purposes. Subjects were given the test product, use instructions and a daily diary. Subjects made the first application at the Testing Facility, under the supervision of a trained technician. Approximately fifteen (15) minutes post-application, all evaluations, instrumental measurements, photographs and replicas were repeated.

Skin replica analyses are presented in a report addendum.

Evaluations of efficacy were based on a comparison of baseline vs. each observation period.

Baseline Evaluations

Panelists reported to the Testing Facility with a freshly washed "clean face" (without wearing face/eye are a cosmetics or having applied any facial skin care products) for baseline visual assessments, photographs and skin replicas. Evaluations were conducted according to the procedures outlined in Section 9.4.

Following all baseline evaluations, subjects were given the product to take home and a daily diary with the following instructions:

Instructions:

The following must be included in this diary:
1. Date and time (a.m. and p.m.) product was used.
2. Any comments or observations you may have had while using the product.
3. DO NOT USE ANY NEW SKIN CARE PRODUCTS OR COSMETICS DURING THE TEST PERIOD.
4. DO NOT USE ANY OTHER FACE CREAMS, FIRMING PRODUCTS OR SKIN TREATMENTS OTHER THAN THE ONE THAT IS PROVIDED.
5. CONTINUE USING YOUR REGULAR MOISTURIZER. DO NOT STOP USING YOUR CURRENT MOISTURIZER OR CHANGE MOISTURIZERS DURING THE STUDY PERIOD.
6. Apply products according to the directions below:

Directions:

Approximately 10-15 minutes after applying your regular moisturizer, apply ½ to 1 dropper full of the test product to your entire face. Rub in until absorbed. Use twice daily (a.m. and p.m.). Avoid getting into eyes. Store at room temperature. Do not store in direct sunlight. Be sure to shake product well before each application.

Fifteen-Minute, and Two- and Four-Week Evaluations

Follow-up evaluations were conducted 15 minutes post-application and after 2 and 4 weeks of product use.

Clinical Evaluation Procedures

Evaluations for all parameters were conducted according to the scales and procedures outlined below.

Fine Line/Wrinkle Evaluation

At each evaluation, a trained technician evaluated the appearance of fine lines and wrinkles at the lateral orbital ("crow's feet") area of the eyes according to the scale below:

Scale for Scoring Fine Lines/Wrinkles
0=None
1-3=Slight
4-6=Noticeable
7-9=Very Noticeable Pore Size Evaluation At each evaluation, a trained technician evaluated pore size on the face of each subject according to the scale below:

Scale for Scoring Pore Size
0=None
1-3=Small-sized pores visible
4-6=Medium-sized pores visible
7-9=Large-sized pores visible Irritation Evaluation At each evaluation, a trained technician evaluated the face of each subject for irritation. This evaluation was for safety purposes only and was not used in determining efficacy.

Scale for Scoring Irritation
0=No irritation present
+=Barely perceptible irritation present
1=Mild irritation present
2=Moderate irritation present
3=Marked irritation present
4=Severe irritation present Cutometer® Evaluation At each visit, a trained technician measured the elasticity of the skin on the face of each subject using the Cutometer®.

Corneometer® Evaluation

At each visit, a trained technician measured the moisture content of the skin on the face of each subject using the Corneometer®.

Visia CR® Complexion Analysis

At all visits, digital images of the face of each subject were taken using the Visia CR® (Canfield Scientific). The images were analyzed using Image Pro® software to determine changes (if any) in the following parameters:

Skin texture;
Skin redness;
Skin radiance; and
Skin evenness

Subject Questionnaire

At the final visit, subjects were required to complete a questionnaire.

Results and Discussion

A total of eight (8/10) test panelists successfully completed the test procedure. Two (2/10) test panelists (Subject Nos. 6 and 7) discontinued for personal reasons unrelated to the conduct of the study.

Daily Dairy Comments

Subjects were given a daily diary to record product use and any pertinent comments.

Visual Evaluation of Crow's Feet Fine Lines/Wrinkles

At each visit, a trained technician evaluated the appearance of crow's feet fine lines/wrinkles on the face of each subject.

The following table presents a summary of mean crow's feet fine lines/wrinkle grading scores.

| Mean Visual Crow's Feet Fine Line/Wrinkle Scores and % Change from Baseline | | |
|---|---|---|
| | Mean Score | Change from Baseline |
| Baseline | 6.8 | — |
| 15 Mins. Post-Appl. | 6.1 | −10.3% |
| 2 Weeks | 6.4 | −5.9% |
| 4 Weeks | 6.1 | −10.3% |

*Statistically significant change from baseline (p < 0.05)

Visual Evaluation of Crow's Feet Fine Lines/Wrinkles (Cont'd)

When measurements taken 15 minutes following a single application and after 2 and 4 weeks of product use were compared with baseline measurements, there was:

a 10.3% improvement (reduction) appearance of crow's feet fine lines/wrinkles 15 minutes post-application and after 4 weeks of product use; and a 5.9% improvement (reduction) in appearance of crow's feet fine lines/wrinkles after 2 weeks of product use.

None of the improvements observed were statistically significant when compared with baseline.

Frequency of Response

The following table presents a summary of the percentage of subjects who had changes in crow's feet fine lines/wrinkles assessed by clinical grading.

| Visual Crow's Feet Fine Line/Wrinkle Evaluation Frequency of Response (% of Subjects with Improvement from Baseline) | | |
| --- | --- | --- |
|  | Improvement | Worsening or No Change |
| 15 Mins. Post-Appl. | 50% | 50% |
| 2 Weeks | 38% | 62% |
| 4 Weeks | 50% | 50% |

When compared with baseline, 50% of the subjects showed improvement 15 minutes post-application and after 4 weeks of product use, and 38% showed improvement after 2 weeks of product use.

Visual Pore Size Evaluation

At each visit, a trained technician evaluated the pore size on the face of each subject.

The following table presents a summary of mean pore size scores.

| Mean Visual Pore Size Scores and % Change from Baseline | | |
| --- | --- | --- |
|  | Mean Score | Change from Baseline |
| Baseline | 6.3 | — |
| 15 Mins. Post-Appl. | 6.3 | 0% |
| 2 Weeks | 6.3 | 0% |
| 4 Weeks | 6.0 | −4.8% |

When measurements taken 15 minutes following a single application and after 2 and 4 weeks of product use were compared with baseline measurements, there was:
no change observed in pore size 15 minutes post-application and after 2 weeks of product use; and
a 4.8% improvement (reduction) in pore size after 4 weeks of product use.

The change in pore size observed after 4 weeks of product use was not statistically significant when compared with baseline.

Frequency of Response

The following table presents a summary of the percentage of subjects who had changes in pore size measurements:

Pore Size Evaluation
Frequency of Response
(% of Subjects with Improvement from Baseline)

|  | Subject Showing | |
| --- | --- | --- |
|  | Improvement | Worsening or No Change |
| 15 Mins. Post-Appl. | 0% | 100% |
| 2 Weeks | 0% | 100% |
| 4 Weeks | 25% | 75% |

When compared with baseline, 25% of subjects showed improvement in pore size scores after 4 weeks of product use.

Irritation Evaluation

At each visit, a trained technician evaluated the irritation on the face of each subject.

The following table presents a summary of mean irritation scores:

Mean Irritation Scores and
% Change from Baseline

|  | Mean Score | Change from Baseline |
| --- | --- | --- |
| Baseline | 0 | — |
| 15 Mins. Post-Appl. | 0 | 0% |
| 2 Weeks | 0 | 0% |
| 4 Weeks | 0 | 0% |

When measurements taken 15 minutes post-application after 2 and 4 weeks of product use were compared with baseline measurements, there was:
no irritation observed on any subject during the course of the study.

Skin Elasticity (Cutometer®) Evaluation

At each visit, a trained technician measured the elasticity of the skin on the face using the Cutometer®.

The following table presents a summary of mean Cutometer® scores:

Mean Cutometer® Scores and
Change from Baseline

|  | Mean Score | Change from Baseline |
| --- | --- | --- |
| Baseline | 0.574 | — |
| 15 Mins. Post-Appl. | 0.570 | −0.7% |
| 2 Weeks | 0.687 | 19.7% |
| 4 Weeks | 0.657* | 14.5% |

*Statistically significant change from baseline ($p < 0.05$)

When measurements taken 15 minutes post-application and after 2 and 4 weeks of product use were compared with baseline measurements, there was:
a 0.7% worsening in the elasticity of the skin 15 following a single application of the test product;
a 19.7% improvement in the elasticity of the skin after 2 weeks of product use; and
a 14.5% improvement in the elasticity of the skin after 4 weeks of product use.

The improvement observed after 4 weeks of product use was statistically significant when compared with baseline.

Frequency of Response

The following table presents a summary of the percentage of subjects who had changes in Cutometer® measurements:

Cutometer® Evaluation
Frequency of Subject Response
(% of Subjects with Improvement from Baseline)

|  | Improvement | Worsening or No Change |
| --- | --- | --- |
| 15 Mins. Post-Appl. | 50% | 50% |
| 2 Weeks | 75% | 25% |
| 4 Weeks | 100% | 0% |

When compared with baseline, 50%, 75% and 100% of the subjects showed improvement in skin elasticity when compared with baseline, at 15 minutes, and after 2 weeks and 4 weeks of use, respectively.

Skin Moisture (Corneometer®) Measurements

At each visit, a trained technician measured the moisture content on the face using the Comeometer®.

The following table presents a summary of mean Corneometer® scores.

Mean Corneometer® Scores and
% Change from Baseline

|  | Mean Score | Change from Baseline |
|---|---|---|
| Baseline | 63.8 | — |
| 15 Mins. Post-Appl. | 62.6 | −1.9% |
| 2 Weeks | 67.9 | 6.4% |
| 4 Weeks | 69.8 | 9.4% |

When measurements taken 15 minutes post-application and after 2 and 4 weeks of product use were compared with baseline measurements, there was:
- a 1.9% worsening (decrease) in the moisture content of the skin 15 minutes post-application;
- a 6.4% improvement (increase) in the moisture content of the skin after 2 weeks of product use; and
- a 9.4% improvement (increase) in the moisture content of the skin after 4 weeks of product use.

The changes observed in the moisture content of the skin were not were statistically significant when compared with baseline, but this lack of significance may be a reflection of the small subject population size.

Frequency of Response

The following table presents a summary of the percentage of subjects who had changes in Corneometer® measurements:

Corneometer® Evaluation
Frequency of Response
(% of Subjects with Improvement from Baseline)

|  | Improvement | Worsening or No Change |
|---|---|---|
| 15 Mins. Post-Appl. | 38% | 62% |
| 2 Weeks | 88% | 12% |
| 4 Weeks | 62% | 38% |

When compared with baseline, 38%, 88% and 62% of the subjects showed improvement in Corneometer® measurements when compared with baseline.

Skin Luminance—VISIA CR® Image Evaluation

At the baseline, Week 2 and Week 4 visits, a trained technician took digital images of the face of each subject. Using ImagePro® software, the images were analyzed to determine changes in skin luminance.

The following table presents a summary of mean luminance scores

Visia CR® Mean Luminance Scores and
% Change from Baseline

|  | Mean Scores | Change from Baseline |
|---|---|---|
| Baseline | 144.48 | — |
| 2 Weeks | 155.71* | 7.8% |
| 4 Weeks | 144.16 | −0.2% |

*Statistically significant change from baseline (p < 0.05)

When measurements taken after 2 and 4 weeks of product use were compared with baseline measurements, there was:
- a 7.8% improvement in skin luminosity after 2 weeks of product use; and
- a 0.2% worsening in skin luminosity after 4 weeks of product use.

The improvement in luminosity observed after 2 weeks of product use was statistically significant when compared with baseline.

Frequency of Response

The following table presents a summary of the percentage of subjects who had changes in skin luminosity:

Skin Image Luminance Analysis
Frequency of Response
(% of Subjects with Change from Baseline)

|  | Improvement | Worsening or No Change |
|---|---|---|
| 2 Weeks | 100% | 0% |
| 4 Weeks | 50% | 50% |

When compared with baseline, 100% and 50% of the subjects showed improvement in skin luminance after 2 and 4 weeks of product, respectively.

Skin Evenness—VISTA CR® Image Evaluation

At the baseline, Week 2 and Week 4 visits, a trained technician took digital images of the face of each subject. Using ImagePro® software, the images were analyzed to determine changes in skin evenness.

The following table presents a summary of mean skin evenness scores.

Skin Image Evenness Analysis and
% of Change from Baseline

|  | Mean Score | Change from Baseline |
|---|---|---|
| Baseline | 116.14 | — |
| 2 Weeks | 98.35 | −15.3% |
| 4 Weeks | 96.38 | −17.0% |

When measurements taken after 2 and 4 weeks of product use were compared with baseline measurements, there was:
- a 15.3% improvement in evenness following 2 weeks of product use; and
- a 17.0% improvement in evenness following 4 weeks of product use The improvements observed in skin evenness after 2 and 4 weeks of product use were not statistically significant when compared with baseline.

Frequency of Response

The following table presents a summary of the percentage of subjects who had changes in skin evenness scores:

Skin Image Evenness Analysis
Frequency of Response
(% of Subjects with Improvement from Baseline)

|  | Improvement | Worsening or No Change |
|---|---|---|
| 2 Weeks | 88% | 12% |
| 4 Weeks | 62% | 38% |

When compared with baseline, 88% and 62% of the subjects showed improvement in skin evenness after 2 and 4 weeks of product, respectively.

Skin Texture—VISIA CR® Image Evaluation

At the baseline, Week 2 and Week 4 visits, a trained technician took digital images of the face of each subject. Using ImageProO software, the images were analyzed to determine changes in skin texture.

The following table presents a summary of mean skin texture scores:
Mean Skin Texture Image Analysis and
% of Change from Baseline

|  | Mean Score | Change from Baseline |
| --- | --- | --- |
| Baseline | 73.42 | — |
| 2 Weeks | 65.55 | −10.7% |
| 4 Weeks | 58.35* | −20.5% |

*Statistically significant change from baseline (p ≤ 0.05)

When measurements taken after 2 and 4 weeks of product use were compared with baseline measurements, there was:
 a 10.8% improvement in skin texture following 2 weeks of product use; and
 a 20.5% improvement in skin texture following 4 weeks of product use
The improvement in skin texture observed after 4 weeks of product use was statistically significant when compared with baseline.

Frequency of Response
The following table presents a summary of the percentage of subjects who had changes in skin texture scores.
Skin Image Texture Analysis
Frequency of Response
(% of Subjects with Improvement from Baseline)

|  | Improvement | Worsening or No Change |
| --- | --- | --- |
| 2 Weeks | 88% | 12% |
| 4 Weeks | 100% | 0% |

After 2 and 4 weeks of product use, 88% and 100% of the subjects, respectively, showed improvement in skin texture.

Figure 2:
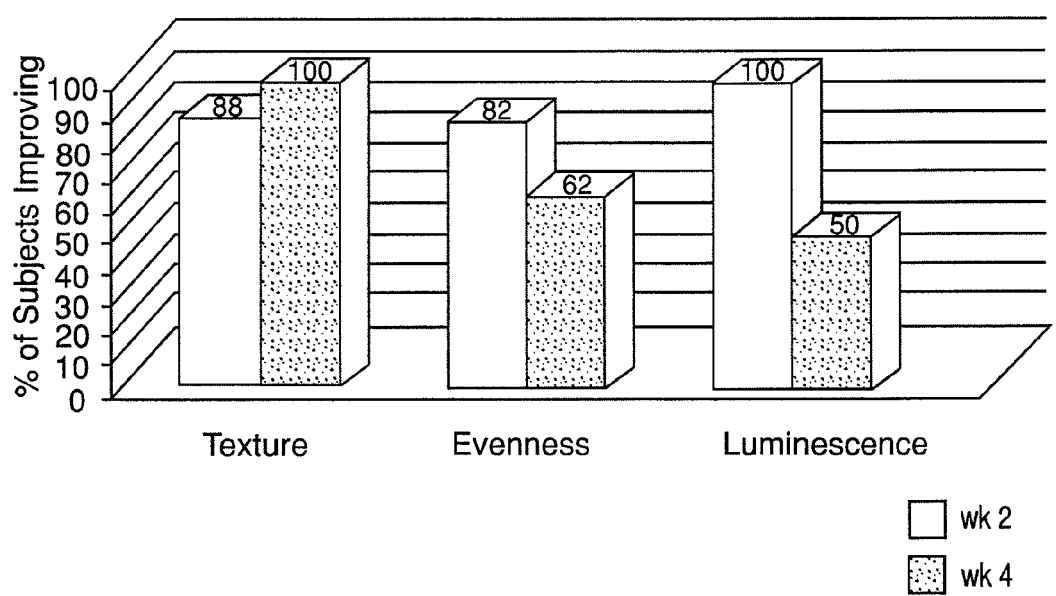
FIG. 2 is a graphical depiction which summarizes the number of subjects showing improvement from baseline in skin texture, evenness and luminance after 2 weeks and 4 weeks after using the product according to the present invention.

A summary chart of the improvements in skin texture, evenness and luminance is presented in FIGS. 1 and 2.

Pore Size-VISIA CR® Image Evaluation
An analysis to determine changes in pore size was conducted using the digital photographs taken with VISIA CRO system at baseline and after 2 and 4 weeks of product use. The photographs were analyzed using ImagePro® software.

The following table presents a summary of mean pore size scores:
Mean Pore Size Image Scores and
% of Change from Baseline

|  | Mean Score | % Improvement Change from Baseline |
| --- | --- | --- |
| Baseline | 14.1 | — |
| 2 Weeks | 8.9 | −36.9% |
| 4 Weeks | 12.2 | −14.5% |

When measurements taken after 2 and 4 weeks were compared with baseline, there was:
 a 36.9% decrease (improvement) in pore size after 2 weeks of product use; and
 a 13.5% decrease (improvement) in pore size after 4 weeks of product use.
The improvements in pore size observed after 2 and 4 weeks were not statistically significant when compared with baseline, but this may reflect the small subject population used.

Frequency of Response
The following table presents a summary of the percentage of subjects who had changes in skin pore scores:
Pore Size Image Analysis
Frequency of Response
(% of Subjects with Improvement from Baseline)

|  | Improvement | Worsening or No Change |
| --- | --- | --- |
| 2 Weeks | 75% | 25% |
| 4 Weeks | 50% | 50% |

When compared with baseline, 75% and 50% of the subjects showed improvement in pore size after 2 and 4 weeks of product use, respectively.

Fine Lines—Visia CR® Image Analysis
An analysis to determine changes in fine lines was conducted using the digital photographs taken with the Visia CRO system at baseline and after 2 and 4 weeks of product use.

Fine Line Visia CR® Evaluation—Area
The following table presents a summary of mean fine line area scores.
Mean Fine Line Image Scores—Area and
% of Change from Baseline

|  | Mean Score | Change from Baseline |
| --- | --- | --- |
| Baseline | 13183.38 | — |
| 2 Weeks | 10905.00 | −17.3% |
| 4 Weeks | 11220.50* | −14.9% |

*Statistically significant difference from baseline, p ≤ 0.05

When measurements taken after 2 and 4 weeks of product use were compared with baseline, there was:
 a 17.3% improvement in fine lines after 2 weeks of product use, and
 a 14.9% improvement in fine lines after 4 weeks of product use.
The improvement observed after 4 weeks of product use was statistically significant when compared with baseline.

The following table presents a summary of the percentage of subjects who had changes in fine line area.
Fine Line Area—Visia CR® Evaluation
Frequency of Response
(% of Subjects with Improvement from Baseline)

|  | Improvement | Worsening or No Change |
| --- | --- | --- |
| 2 Weeks | 75% | 25% |
| 4 Weeks | 100% | 0% |

When compared with baseline, 75% and 100% of the subjects showed improvement after 2 and 4 weeks of product use, respectively.

Fine Line Visia CR® Evaluation—Length
The following table presents a summary of mean fine line length scores.
Mean Fine Line Image Scores—Length and
% of Change from Baseline

| | Mean Score | Change from Baseline |
|---|---|---|
| Baseline | 2103.59 | — |
| 2 Weeks | 1763.56 | −16.2% |
| 4 Weeks | 1863.95 | −11.4% |

When measurements taken after 2 and 4 weeks of product use were compared with baseline, there was:
- a 16.2% improvement (decrease) in the length of fine lines after 2 weeks of product use; and
- an 11.4% improvement (decrease) in the length of fine lines after 4 weeks of product use.

The improvements observed after 2 and 4 weeks of product use were not statistically significant when compared with baseline.

The following table presents a summary of the percentage of subjects who had changes in the fine line length:
Fine Line Length—Visia CR® Evaluation
Frequency of Response
(% of Subjects with Improvement from Baseline)

| | Improvement | Worsening or No Change |
|---|---|---|
| 2 Weeks | 75% | 25% |
| 4 Weeks | 75% | 25% |

When compared with baseline, 75% of the subjects showed improvement after 2 and 4 weeks of product use.

Fine Line Visia CR® Evaluation—Density

The following table presents a summary of mean fine line density scores:
Fine Line Density—Visia CR® Evaluation and
% of Change from Baseline

| | Mean Score | Change from Baseline |
|---|---|---|
| Baseline | 204.79 | — |
| 2 Weeks | 204.86 | 0% |
| 4 Weeks | 202.99 | −0.9% |

When measurements taken after 2 and 4 weeks of product use were compared with baseline, there was:
- no change in fine line density after 2 weeks of product use; and
- a 0.9% improvement in fine line density after 4 weeks of product use.

The change in fine line density observed after 4 weeks of product use was not statistically significant when compared with baseline.

The following table presents a summary of the percentage of subjects who had changes in fine line density:
Fine Line Density—Visia CR® Evaluation
Frequency of Response
(% of Subjects with Improvement from Baseline)

| | Improvement | Worsening or No Change |
|---|---|---|
| 2 Weeks | 50% | 50% |
| 4 Weeks | 62% | 38% |

When compared with baseline, 50% and 63% of the subjects showed improvement after 2 and 4 weeks of product use.

Comparison of Bioglass Serum-VY 134 (the Inventive Formulations Title) Results with Marketed Products The results obtained with Bioglass Serum-VY 134 (a preferred embodiment of the present invention) are typical and in some case surpass the results reported with other skin treatment products. The following represents reported treatment results from several marketed products:

Nu Skin 180°® 8-Week Clinical Study (50 subjects) reported with Clinical Grading:
- 66% of subjects experienced a decrease in discoloration;
- 70% of subjects experienced a decrease in pores; and
- 80% of subjects experienced a decrease in wrinkles.

Prevage® MD in a 6-week clinical study conducted with 21 subjects reported:
- 29% reduction in the appearance of fine lines and wrinkles;
- 26% reduction in skin roughness and dryness;
- 37% increase in skin hydration; and
- 33% improvement in skin's overall appearance.

Prevagen® Anti-Aging Treatment 8-week study with 0.5% Idebenone achieved the following results:*
- 36% improvement in the appearance of fine lines and wrinkles;
- 47% improvement in skin tone;
- 55% improvement in the overall appearance of photo-damaged skin;
- 63% improvement in the look of skin's firmness/elasticity; and
- 77% improvement in the appearance of rough/dry skin.

REVERSE in an 8-week study was associated with:
- 98% of subjects showed visible improvement in brightness;
- 30% of subjects showed visible reduction in fine lines; and
- 98% of subjects reported a smoother skin texture.

The RevitaCel System (RevitaCel skin care regiment, consisting of the Berryhydroxy Blast (an AHA marketed product) followed by the RevitaCel/Human Fibroblast product, and the addition of a marketed moisturizer; a three-step application process) used for 3 months showed:
- over 60% reduction in wrinkle reduction;
- over 70% reduction in fine lines; and
- over 40% reduction in depth of wrinkles.

Skin Works: Anti-Aging Skin Care with Glucosamine Complex was associated with the following results after 4 weeks of use:
- more than 40% increase in skin smoothness; and
- 23% increase in skin firmness.

And after 3 months of regular usage of glucosamine complex, women showed:
- 57% improvement in fine lines and wrinkles;
- 55% Reduction in wrinkle depth;
- 51% Improvement in skin moisture content; and
- 45% Improvement in skin luminosity and clarity.

Pro+Therapy Advanced Repair Serum containing Zeatin was tested in a group of 30 subjects. Expert assessment of results with daily topical application of 0.1% Zeatin revealed the following after 4 weeks of use:
- 52% improvement in the appearance of skin roughness;
- 18% improvement of the appearance of fine lines and wrinkles;
- 9% reduction in the appearance of mottled hyperpigmentation.

And after 12 weeks of use:
- 86% improvement in the appearance of skin roughness;
- 34% improvement at the appearance of fine lines and wrinkles;

32% reduction in the overall severity of the visible signs of aging; and

33% improvement in the visible appearance of skin lesions.

TimeWise® Miracle Set in clinical testing showed on average after 8 weeks of continued use:

56% reduction in the appearance of fine lines and wrinkles;

37% increase in skin firmness.

Photomodulation treatment (Laser treatment) has been associated with:

a 62% global improvement in the appearance of skin in the eye area

26% improvement in skin roughness;

30% improvement in elastosis (or yellow, irregularly-thickened skin);

14% improvement in pore size;

25% improvement in redness.

Figure 3:
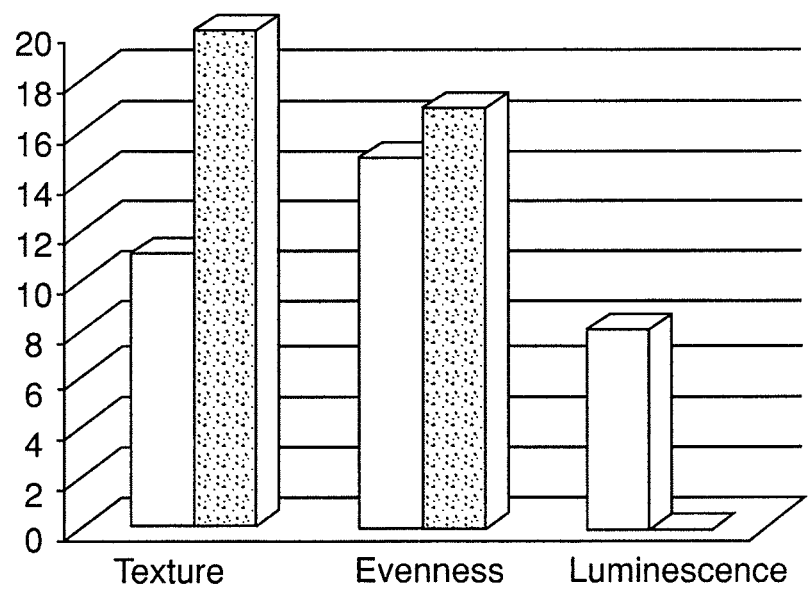
FIG. 3 is a graphical depiction which summarizes percentage improvement in skin texture, evenness and luminance after 2 weeks and 4 weeks after using the product according to the present invention.

A summary of these reported results and those obtained with Bioglass Serum-VY 134 (a preferred embodiment of the present invention) are presented in FIG. 3.

A summary of these results compared to the results of Bioglass Serum-VY 134 (a preferred embodiment of the present invention) are presented below:

Summary of Bioglass Serum-VY 134 (the Inventive Formulation) and Marketed Product Effectiveness

|  | Bioglass (our Formulation) | Competitors | Laser modulation |
|---|---|---|---|
| Pore Size Subjects |  |  |  |
| Improving | 75% in 2 wks | 70% in 8 wks |  |
| Improvement | 37% in 2 wks |  | 14% |
| Elasticity Subjects |  |  |  |
| Improving | 100% in 4 wks | 37-70% in 8 wks |  |
| Improvement | 20% in 2 wks | 23% in 4 wks |  |
|  | 15% in 4 wks |  |  |
| Fine Lines Subjects |  |  |  |
| Improving | 88% in 2 wks | 30-80% in 8 wks |  |
| Improvement | 37% in 4 wks | 18% in 4 wks |  |
|  |  | 36-56% in 8 wks |  |
|  |  | 34-70% in 12 wks |  |
| Texture Subjects |  |  |  |
| Improving | 100% in 4 wks | 77-98% in 8 wks |  |
| Improvement | 21% in 4 wks | 40% in 4 wks | 26% |
| Skin Color Subjects |  |  |  |
| Improving | 100% in 2 wks | 66-98% in 8 wks |  |
| Improvement | 8% in 2 wks | 45% in 12 wks | 25% |

*Statistically significant ($p < 0.05$) improvement from baseline.

At the final visit, subjects were required to respond to a questionnaire.

The following table presents a summary of questionnaire responses:

Questionnaire Responses

| Since using the test product, | Extremely Noticeable to Noticeable Improvement | Slight Improvement to No Change |
|---|---|---|
| Do you notice a decrease in fine lines/wrinkles at the crow's feet area? | 100% | 0% |
| Do you notice a decrease in pore size? | 100% | 0% |
| Do your skin feel softer and smoother? | 100% | 0% |
| Does you skin feel "firmer" or "Tighter"? | 100% | 0% |
| Does you skin appear more radiant? | 87% | 13% |
| Does you skin feel hydrated? | 100% | 0% |

| After using the product, | Agree | Disagree or No Opinion |
|---|---|---|
| My skin appears healthier: | 100% | 0% |
| Areas of redness have decrease on my face: | 75% | 25% |
| My skin tone appears more even: | 100% | 0% |
| I feel the overall quality of my skin has: | 100% | 0% |

|  | Yes | No |
|---|---|---|
| Would you purchase this product? | 100% | 0% |
| Would you recommend this product to a friend? | 100% | 0% |

All of the subjects (100%) responded they noticed a decrease in fine lines/wrinkles, a decrease in pore size, softer, smoother, and tighter skin. Additionally, the subjects (87-100%) reported their skin appeared more radiant and 100% of subjects responded their skin appeared healthier, more even and that the overall quality of their skin improved.

Conclusions

A 4-week take-home use study was conducted with 8 female subjects who were graded to have at least moderately aged or more severe skin. Subjective and visual technical grading, along with in situ image analysis were used to document improvements in skin aging parameters after just 2 weeks of product. Continuing improvement was observed in most skin parameters at the 4-week evaluation. The following mean improvements were observed.

- a statistically significant (21%) improvement in skin texture, with up to 100% of subjects improving;
- a statistically significant improvement in skin elasticity (15-20%), with up to 100% of subjects improving;
- 15-17% improvements in fine lines and wrinkles, with up to 100% of subjects improving;
- 37% improvement in pore size, with 75% of subjects improving; and
- 6-9% improvements in skin moisture, with 62-88% subjects improving.

Up to 100% of the subjects responded with improvements in at least one or more skin aging parameters and 100% of subjects felt their skin showed improvements in fine lines/wrinkles, pore size, softness, smoothness, skin tightness, evenness, overall skin quality and healthiness.

Example 2

In accordance with another study, the following was determined using the formulation set out below:

The samples were used on six different patients after one jet peel exfoliation and five who had no pre-treatment. The formulation of the invention penetrated very well on both sets of patients but appeared to penetrate somewhat faster on those who had been exfoliated. The redness caused by the Jet Peel resolved quicker than usual with the use of the formulation of the invention.

All of the subjects were impressed with the feel and smoothness of the skin. Immediately after application the skin feels well hydrated but some drying still occurs after a time and moisturizers are required. This obviously results from the removal of some corneum (perhaps a moisturizer incorporating hyaluronan plus bioactive microparticulates might be something to consider later).

Formulation Used

| | |
|---|---|
| Purified water | 97.1% |
| Sodium Hyaluronate | 0.5% (molecular weight in the order of above 700 kiloDaltons) |
| Calcium Sodium Phosphosilicate | 0.95% |
| Citric Acid | 0.9% |
| Mica | 0.05% |
| Methyl parabens/phenoxyethanol | 0.5% |

With respect to the above description, it is to be understood by the person skilled in the art that the dimensional relationships for the parts of the invention, include obvious variations of materials, form, function and manner of operation, assembly and use, and therefrom all equivalent relationships to those described in the specification are intended to be encompassed by the present invention.

Therefore, the foregoing is considered as illustrative only of the principles of the invention. Further, since numerous modifications and changes will readily occur to those skilled in the art, the invention is not limited to the exact construction and operation shown and described, and accordingly, all suitable modifications and equivalents that may be resorted to, fall within the scope of the invention.

Thus, it is to be understood that the invention is not limited in its application to the details of construction and to the arrangements of the components set forth in the above description. The invention is capable of other embodiments and of being practiced and carried out in various ways. Also, it is to be understood that the phraseology and terminology employed herein are for the purpose of exemplification and should not be regarded as limiting.

The invention claimed is:

1. An acidic topical cosmetic composition compatitble with the skin comprising: at least one compound selected from bioactive/biocompatible microparticulates (ceramics/glass); and an intradermal delivery vehicle in an amount sufficient to facilitate deposition and penetration of said bioactive microparticulates through tissue at a site to be treated wherein the intradermal delivery vehicle is selected from the group consisting of: hyaluronans, hyaluronic acid and/or salts thereof and/or fragments and subunits of hyaluronic acid having an average molecular weight of about 700 KiloDaltons wherein the pH of the composition is 5.2 to 5.5.

2. The composition according to claim 1 wherein the intradermal delivery vehicle is selected from the group consisting of hyaluronic acid and a salt thereof.

3. The composition according to claim 1 wherein the hyaluronic acid is of medical grade and has an average molecular weight of about 700 kiloDaltons and the composition includes citric acid.

4. A composition according to claim 1, 2 or 3 wherein the bioactive multiparticulates comprise a bioactive glass selected from a bioactive glass comprising 60 mol % $SiO_2$, 36 mol % CaO and 4 mol % $P_2O_5$ and a bioactive glass comprising 70 mol % $SiO_2$ and 30 mol % CaO and wherein the form of hyaluronic acid is hyaluronic acid having a molecular weight of about 700 kiloDaltons.

5. An acidic topical cosmetic composition compatible with the skin whose pH is 5.2-5.5, the composition comprising hyaluronan and bioactive microparticulates (ceramics/glass), the microparticulates selected from the group consisting of: bioactive glass, bioactive ceramics, bioactive minerals and/or composites of these, the hyaluronan comprising medical grade hyaluronic acid, having an average molecular weight about 700 kiloDaltons.

6. The cosmetic composition according to claim 5 wherein the bioactive glass comprises: 45% by weight Silicon Dioxide, 24.5% by weight Calcium Oxide, 24.5% by weight Disodium Oxide and 6% by weight Diphospho pentoxide and which bioactive glass is less than 20 micrometers in diameter, the composition including citric acid.

7. The composition of claim 1, 2 or 3 wherein the form of hyaluronic acid comprises at least 10 mg of the form of hyaluronic acid per square inch.

8. A method of cosmetically treating skin comprising administering to the skin an effective amount of a composition of claim 1, 2 or 3.

9. The method of claim 8 wherein the method is for cosmetically treating skin after non-ablative skin rejuvenation procedures.

10. The method of cosmetically treating skin of claim 8 wherein the method is for accomplishing at least one of the following:

reduce inflammation of skin tissue;
enhance and accelerate healing of skin tissue;
inhibit infection of skin tissue;
enhance skin tone; and
moisturize.

11. An acidic cosmetic composition comprising about 96.6% water; 0.5% sodium hyaluronate molecular weight in the order of about 700 kiloDaltons; 0.95% calcium sodium phosphosilicate; 0.9% citric acid; 0.8% phenoxyethanol; and 0.05% mica wherein the pH of the composition is 5.2 to 5.5.

12. An acidic topical cosmetic composition compatible with the skin whose pH is 5.2-5.5, the composition suitable for the topical treatment of skin, said composition comprising at least one compound selected from the group consisting of bioactive microparticulates, and an intradermal delivery vehicle selected from the group consisting of: hyaluronans, hyaluronic acid and/or salts thereof, fragments and subunits of hyaluronic acid having an average molecular weight of 700 KiloDaltons and being in an amount sufficient to facilitate the bioactive microparticulates deposition and penetration through the tissue (including scar tissue) at the site to be treated.

13. The composition according to claim 12 comprising hyaluronic acid or a salt thereof, the microparticulates comprising ceramics/glass microparticulates and including citric acid.

14. The composition according to claim 12 or 13 wherein the hyaluronic acid is medical grade and has an average molecular weight of about 700 kiloDaltons.

15. The composition according to claim 12, 13 or 14 wherein the bioactive multiparticulates are a bioactive glass comprising 60 mol % $SiO_2$, 36 mol % CaO, and 4 mol % $P_2O_5$.

16. The composition according to claim 12, 13 or 14 wherein the bioactive multiparticulates comprise bioactive glass which bioactive glass comprise 70 mol % $SiO_2$, 30 mol % CaO.

17. An acidic cosmetic composition comprising hyaluronan and bioactive ceramics/glass microparticulates, said bioactive microparticulates selected from the group consisting of: bioactive glass, bioactive ceramics, bioactive minerals and/or composites of these, the hyaluronan comprising medical grade hyaluronic acid, having an average molecular weight about 700 kiloDaltons.

18. The composition of claim 17 wherein the bioactive microparticulates are bioactive glass which are comprised of 45% wt Silicon Dioxide, 24.5% wt Calcium Oxide, 24.5% wt Disodium Oxide and 6% wt Diphospho pentoxide and which bioactive glass is less than 20 micrometers in diameter, the composition comprising a small amount of citric acid.

19. An effective amount of the composition of claim 12 or 13 wherein the form of hyaluronic acid comprises at least 10 mg of the form of hyaluronic acid.

20. An effective amount of the composition of claim 17 or 18 wherein the form of hyaluronic acid comprises at least 10 mg of the form of hyaluronic acid.

21. A method of treating skin comprising administering to the skin an effective amount of a composition according to claim 12.

22. A method of treating skin comprising administering to the skin an effective amount of a composition according to claim 17 or 18.

23. The method of treating skin according to claim 21 wherein the method is for treating skin after non-ablative skin rejuvenation procedures.

24. The method of treating skin according to claim 23 wherein the method is for treating skin after non-ablative skin rejuvenation procedures.

25. The method of treating skin according to claim 22 wherein the method is for accomplishing at least one of the following:
reduce inflammation of skin tissue;
enhance and accelerate healing of skin tissue;
inhibit infection of skin tissue;
enhance skin tone; and
moisturize.

26. The method of treating skin according to claim 22 wherein the method is for accomplishing at least one of the following:
reduce inflammation of skin tissue;
enhance and accelerate healing of skin tissue;
inhibit infection of skin tissue;
enhance skin tone; and
moisturize.

27. A stable acidic topical cosmetic composition compatible with the skin for administration to the human skin comprising of purified water 97.1%, Sodium Hyaluronate 0.5% (molecular weight in the order of about 700 kilo Daltons), Calcium Sodium Phosphosilicate 0.95%, Citric Acid 0.9%, Mica 0.05%, and preservative 0.5% wherein the pH of the composition is 5.2 to 5.5.

28. A stable acidic topically applicable cosmetic composition for administration to the human skin comprising purified water 97.1%, Sodium Hyaluronate 0.5% (molecular weight in the order of about 700 kiloDaltons), Calcium Sodium Phosphosilicate 0.95%, Citric Acid 0.9%, Mica 0.05%, and Caprylyl Glycol 0.5% and having a pH of 5.2-5.5.

29. A stable acidic composition compatible with the skin for administration to the human skin comprising of water 96.6%, Sodium Hyaluronate molecular weight in the order of about 700 kiloDaltons; 0.5%, Calcium Sodium Phosphosilicate 0.95%, Citric Acid 0.9%, Phenoxyethanol 0.8%, another preservative 0.2%, and Mica 0.05% wherein the pH of the composition is 5.2 to 5.5.

30. A method of treating human skin comprising administering to the skin an effective amount of the composition claimed in claim 27.

31. A method of treating human skin comprising administering to the skin an effective amount of the composition claimed in claim 28.

32. A method of treating human skin comprising administering to the skin an effective amount of the composition claimed in claim 29.

33. A stable acidic topically applicable cosmetic composition compatible with the skin having a pH in the order of 5.2-5.5, the composition comprising a bioactive/biocompatible microparticulate and an intradermal delivery vehicle selected from medical grade hyaluronic acid which has an average molecular weight of about 700 kiloDaltons and further comprising a small amount of a weak organic acid.

34. A composition according to claim 33 wherein the bioactive multiparticulates comprise a bioactive glass comprising 60 mol % $SiO_2$, 36 mol % CaO and 4 mol % $P_2Os$ and the weak organic acid comprises citric acid.

35. A composition according to claim 33 wherein the bioactive glass mutliparticulates comprises a bioactive glass comprising 70 mol % $SiO_2$ and 30 mol % CaO and the weak organic acid comprises citric acid.

36. An effective amount of the composition of claim 33 wherein the hyaluronic acid or salt thereof comprises at least 10 mg of the form of hyaluronic acid per square inch.

37. A method of treating skin comprising administering to the skin an effective amount of a composition of claim 33.

38. The method according to claim 37 wherein the method is for treating skin after non-ablative skin rejuvenation procedures.

39. The method according to claim 37 wherein the method is for accomplishing at least one of the following:
   reduce inflammation of skin tissue;
   enhance and accelerate healing of skin tissue;
   inhibit infection of skin tissue;
   enhance skin tone; and
   moisturize.

40. A method of treating skin comprising administering to the skin an effective amount of a composition of claim 2.

41. A method of treating skin comprising administering to the skin an effective amount of a composition of claim 3.

* * * * *